Figure 1:
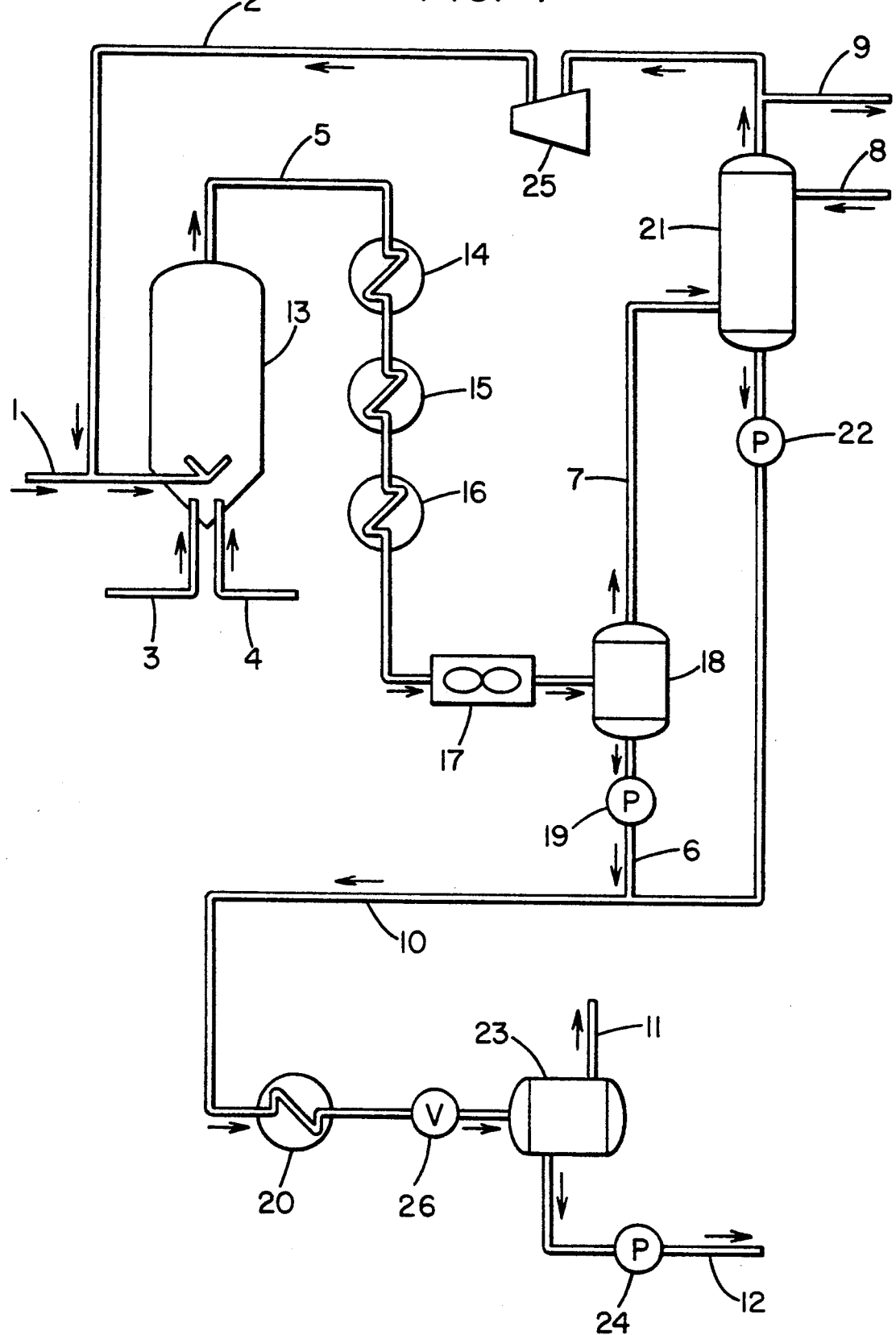

United States Patent [19]

Benkalowycz et al.

[11] Patent Number: 5,300,684
[45] Date of Patent: Apr. 5, 1994

[54] PROCESS FOR THE FLUIDIZED BED OXIDATION OF ETHANE TO ACETIC ACID

[75] Inventors: Nancy C. Benkalowycz, Westlake; Patricia R. Blum, Macedonia; David R. Wagner, Chesterland, all of Ohio

[73] Assignee: The Standard Oil Company, Cleveland, Ohio

[21] Appl. No.: 803,882

[22] Filed: Dec. 9, 1991

[51] Int. Cl.$^5$ .............................................. C07C 51/16
[52] U.S. Cl. ........................................................ 562/547
[58] Field of Search ............................................ 562/549

[56] References Cited

U.S. PATENT DOCUMENTS 3,948,983  4/1976  Hackmann et al. ............. 560/533 R
5,162,578  11/1992 McCain et al. .................. 562/512.2

OTHER PUBLICATIONS

Reactions of Pure Hydrocarbons, Egloff, (ACS Monograph Series #73) (1937) pp. 99–111 and 146.
Solomon's, Organic Chemistry, 2nd Ed., p. 266.

Primary Examiner—José G. Dees
Assistant Examiner—Joseph M. Conrad, III
Attorney, Agent, or Firm—Charles S. Lynch; Michael F. Esposito; David J. Untener

[57] ABSTRACT

Disclosed is a process for oxidizing ethane to acetic acid which comprises feeding ethane and a recycle gas to a fluidized bed reaction zone containing fluidized particulate solid oxidation catalyst, feeding a molecular oxygen-containing gas separately from said ethane to said reaction zone so that said molecular oxygen-containing gas first mixes with the major portion of the combustible hydrocarbon feed gases within the fluidized bed, said process including the steps of (1) cooling the gaseous effluent from the reaction zone, (2) separating most of the acetic acid in liquid form from the effluent gases, leaving a gaseous stream containing nearly all of the carbon oxides contained in said effluent, (3) purging a small portion of said gaseous stream and recycling most of said gaseous stream as part of the feed to said reaction zone, wherein said purging serves to prevent build-up of carbon oxides in the reaction zone, and said recycling serves to maintain a high proportion of carbon oxides in said reaction zone gases, thus aiding in moderating the temperature elevating effect of the highly exothermic oxidation reaction in said reaction zone.

3 Claims, 1 Drawing Sheet

PROCESS FOR THE FLUIDIZED BED OXIDATION OF ETHANE TO ACETIC ACID

This invention relates to an improved process for the oxidation of ethane to acetic acid.

The use of catalyst systems for the gas phase oxidation (dehydrogenation in the presence of oxygen) of ethane to ethylene and acetic acid has been known. In 1978, Union Carbide Corporation published a report in the Journal of Catalysis describing a fixed bed ethane oxydehydrogenation to ethylene process. Several U.S. Pat. Nos. (4,250,346, 4,524,236, 4,568,790, 4,899,003 and 4,596,787) have been granted on low temperature oxydehydrogenation of ethane to ethylene. An envisioned commercial process is shown in an article in The Arabian Journal for Science and Engineering, Vol 10, No 4, pp. 353–360, by Brockwell and Kendall, as well as in 4,899,003. Acetic acid was a reported co-product of the Union Carbide process.

Some of these Carbide references mention feed diluents, such as nitrogen or carbon oxides, but none of the references suggests (1) first mixing oxygen and ethane within a fluidized bed reactor (2) recycling most of the reactor effluent, after separation of product acetic acid, to the reactor to help control the temperature rise caused by a highly exothermic oxidation reaction by maintaining a high concentration of carbon oxide diluents in the reactor and (3) purging a small portion of the reactor effluent remaining after removal of acetic acid product to prevent continual build-up of carbon oxides in the system and at the same time obviating the *separation* of carbon oxides from ethylene, etc., including the very costly cryogenic separation of carbon monoxide.

Most of the references do not even show an overall plant processing scheme, but the Brockwell and Kendall publication shows on page 353 an overall flow chart in which $CO_2$ and CO are separately removed and only unreacted ethane is recycled to the reactor. The same is true of U.S. Pat. No. 4,899,003. Of course in the various Carbide publications, the main product is ethylene and acetic acid is only a by-product.

It is an object of the present invention to provide an improved, economical process for the production of acetic acid by the catalytic oxidation of ethane.

Other objects, as well as aspects, features and advantages, of the present invention will become apparent from the disclosure which follows:

In accordance with the present invention there is provided a process for oxidizing ethane to acetic acid which comprises feeding ethane and a recycle gas to a fluidized bed reaction zone containing fluidized particulate solid oxidation catalyst, feeding a molecular oxygen-containing gas separately from said ethane to said reaction zone so that said molecular oxygen-containing gas first mixes with the major portion of the combustible hydrocarbon feed gases within the fluidized bed, said process including the steps of (1) cooling the gaseous effluent from the reaction zone, (2) separating most of the acetic acid in liquid form from the effluent gases, leaving a gaseous stream containing nearly all of the carbon oxides contained in said effluent, (3) purging a small portion of said gaseous stream and recycling most of said gaseous stream as part of the feed to said reaction zone, wherein said purging serves to prevent build-up of carbon oxides in the reaction zone, and said recycling serves to maintain a high proportion of carbon oxides in said reaction zone gases, thus aiding in moderating the temperature elevating effect of the highly exothermic oxidation reaction in said reaction zone.

Compared to prior art processes for oxidation of ethane to acetic acid as the prime product, the present process makes it possible readily to carry out such reaction in a single step in a single reaction zone or reactor in an economic manner which provides for the heat transfer requirements of this highly exothermic reaction.

The present invention utilizes the heat transfer advantages of a fluidized bed reactor, aided by the dilution effect of the recycled carbon oxides, for the essentially isothermal reaction of ethane to acetic acid. Internal cooling coils within the fluidized bed can maintain the desired reaction temperature and can be used to generate utility steam. The backmixing characteristics of a fluidized bed reactor enhances the selectivity of conversion to acetic acid in preference to ethylene. Most important is that all mixing of highly exothermically reacting ethane with molecular oxygen takes place within the fluidized bed where oxygen, as well as the ethane, are diluted by the solid catalyst and by the relatively inert recycle gas stream, thus allowing the use of higher concentrations of oxygen within the bed than would be safe were the feed and oxygen premixed before being introduced into the reaction zone. Moreover, as the reaction is oxygen limited, the increased oxygen feed to the reactor provides for potentially higher ethane and ethylene conversions than can be achieved with a fixed bed reactor.

The purge prevents build-up of inerts within the process, carbon dioxide removal and low temperature (cryogenic) gas separation systems are not required. This elimination of costly carbon dioxide removal equipment and the elimination of even more costly cryogenic carbon monoxide separation equipment results in substantial process cost reduction.

The pressure utilized in the fluidized bed reaction zone is usually from 250 to 450 psig, and the reaction zone temperature is usually from 200° to 400° C.

FIG. 1 represents one arrangement of apparatus for carrying out the process of invention. Ethane feed in line 1 is joined by a recycle stream containing water, CO, $CO_2$, $O_2$, ethylene and ethane in line 2, and the combined stream is fed to fluidized bed reactor 13 containing a fluidized bed of particulate catalyst. Separately, a molecular oxygen-containing stream through line 3 and steam through line 4 are introduced into the fluidized bed. The hot oxidation product effluent flows through line 5 through steam generator heat exchanger 14, and coolers 15 and 16 and air cooler 17 to separator drum 18. The partially condensed effluent from 17 flows into 18 from which liquid comprising water and acetic acid-flows through line 6, pump 19 and line 10 to heat exchanger 20.

The overhead gaseous effluent in line 7 from knockout drum 18 enters the lower end of absorption column 21. The stream in line 6 is mainly acetic acid and water vapors. Most of the acetic acid entering 21 is absorbed by the water countercurrently flowing in 21 and introduced through line 8. The aqueous acid stream leaves the bottom of 21 and is conveyed by pump 22 through line 10 where it is joined by the aqueous acid stream in line 6 and passes through 20 and thence to flash separator 23 through valve 26. The bulk of the acetic acid in water is pumped from the bottom of the separator 23 by pump 24 through line 12 as product. A small purge stream exits 23 through line 11 and is mainly $CO_2$.

The gaseous effluent from the top of absorber 21 comprising mainly CO, $CO_2$, water and ethane is recycled to the reactor 13 by compressor 25 through line 2. A small portion of such effluent, usually 0.4 weight percent to 3 weight percent, is purged from the system through line 9.

The particular heat exchangers are not part of the invention, except to the extent that 14, 15, 16 and 17 is simply one illustration of apparatus for effecting the step of the claims of "cooling the gaseous effluent". Exchangers 14, 15, 16 and 20 are indirect heat exchangers in which the cooling fluid entering is water, while indirect heat exchanger 17 is an air cooler. Moreover, the fluidized bed in reactor 13 contains cooling coils (not shown) in the bed into which water is introduced and from which steam exits. In the arrangement shown 14 also produces steam. Such steam can be utilized to generate power or in any other suitable way.

In a specific example of the process of the present invention, the catalyst in the fluidized bed in reactor 13 has the empirical formula:

$$Mo_{0.37}Re_{0.25}V_{0.26}Nb_{0.07}Sb_{0.03}Ca_{0.02}O_x$$

This catalyst is made in the manner described for Catalyst (VIII) in EPA 407,091 (Kitson). This specific example is summarized in Table 1 wherein the stream numbers are the same as the numbers in the lines in FIG. 1, and the process is operated according to the description of FIG. 1. In this example the temperature in the fluidized bed in reactor 13 is about 500° C. and the pressure in the bed is about 400 psig. The internal diameter of the reactor 13 is 17 feet. Table 1 also shows the temperatures and pressures in lines 1 through 12. The amounts in Table 1 are all in lb. moles/hour.

It will be seen from this example that the ultimate yield of acetic acid in this recycle process, based on fresh ethane plus ethylene fed to the reactor, is very high, even with the losses which occur because of the purge stream.

Other ethane oxidation catalysts useful in the process of this invention include for example the catalysts of the aforesaid EPA 407,091 and the catalysts disclosed in U.S. Pat. No. 4,250,346.

As will be evident to those skilled in the art, various modifications of this invention can be made or followed in the light of the foregoing disclosure and discussion without departing from the spirit and scope of the disclosure or from the scope of the claims.

What we claim is:

1. A process for oxidizing ethane to acetic acid which comprises feeding ethane and a recycle gas to a fluidized bed reaction zone containing fluidized particulate solid oxidation catalyst, feeding a molecular oxygen-containing gas separately from said ethane to said reaction zone so that said molecular oxygen-containing gas first mixes with the major portion of the combustible hydrocarbon feed gases within the fluidized bed, said process including the steps of (1) cooling the gaseous effluent from the reaction zone, (2) separating most of the acetic acid in liquid form from the effluent gases, leaving a gaseous stream containing nearly all of the carbon oxides contained in said effluent, (3) purging a small portion of said gaseous stream and recycling most of said gaseous stream as part of the feed to said reaction zone, wherein said purging serves to prevent build-up of carbon oxides in the reaction zone, and said recycling serves to maintain a high proportion of carbon oxides in said reaction zone gases, thus aiding in moderating the temperature elevating effect of

TABLE 1

| | Stream No. | | | | | |
|---|---|---|---|---|---|---|
| | 1 | 2 | 3 | 4 | 5 | 6 |
| | Stream Name | | | | | |
| Component | Ethane Feed | Recycle Gas | Oxygen Feed | Process Water | Reactor Effluent | Separator Bottoms |
| Water | 0 | 2064.5 | 0 | 710.2 | 4041.1 | 1395.5 |
| Carbon Monoxide | 0 | 6514.7 | 0 | 0 | 6588.0 | 2.0 |
| Carbon Dioxide | 0 | 10597 | 0 | 0 | 10751 | 19.7 |
| Oxygen | 0 | 8.4 | 1769.2 | 0 | 8.5 | 0 |
| Ethylene | 21.5 | 83.1 | 0 | 0 | 84.0 | 0.006 |
| Ethane | 1074.0 | 3261.5 | 0 | 0 | 3295.0 | 0.11 |
| Acetic Acid | 0 | 1.1 | 0 | 0 | 944.6 | 445.0 |
| Ethanol | 0 | 1.9 | 0 | 0 | 3.2 | 0.38 |
| Ethyl Acetate | 0 | 8.7 | 0 | 0 | 10.2 | 0.59 |
| Temperature (F) | 100 | 273 | 100 | 267 | 500 | 280 |
| Pressure (psig) | 400 | 400 | 400 | 400 | 400 | 383 |
| | Stream No. | | | | | |
| | 7 | 8 | 9 | 10 | 11 | 12 |
| | Stream Name | | | | | |
| Component | Separator Overhead | Absorber Water | Recycle Gas Purge | Wet Acid | Product Purge | Wet Acid Product |
| Water | 2645.6 | 6663.4 | 20.8 | 8619.1 | 4.7 | 8614.4 |
| Carbon Monoxide | 6586.0 | 0 | 65.8 | 7.4 | 7.2 | 0.18 |
| Carbon Dioxide | 10732 | 0 | 107.0 | 46.9 | 39.2 | 7.6 |
| Oxygen | 8.5 | 0 | 0.08 | 0.001 | 0.001 | 0 |
| Ethylene | 84.0 | 0 | 0.84 | 0.029 | 0.029 | 0 |
| Ethane | 3294.9 | 0 | 32.9 | 0.52 | 0.52 | 0.003 |
| Acetic Acid | 499.6 | 0 | 0.011 | 943.5 | 0.34 | 943.1 |
| Ethanol | 2.8 | 0 | 0.02 | 1.19 | 0.006 | 1.2 |
| Ethyl Acetate | 9.6 | 0 | 0.08 | 1.41 | 0.039 | 1.4 |
| Temperature (F) | 280 | 100 | 255 | 278 | 114 | 114 |
| Pressure (psig) | 378 | 388 | 373 | 383 | 0 | 7.056 | the highly exothermic oxidation reaction in said reaction zone.

2. A process of claim 1 wherein the pressure in the fluidized bed reaction zone is in the range from 250 to 450 psig.

3. A process of claim 2 wherein the temperature in the fluidized bed reaction zone is in the range from 200° to 400° C.

* * * * *